United States Patent [19]

Owens et al.

[11] Patent Number: 4,761,143
[45] Date of Patent: Aug. 2, 1988

[54] ELECTRODE CLIP

[76] Inventors: Rick L. Owens, 3078 Thunder Bay Rd., Little Canada, Minn. 55117; Michael J. Fowler, 649 Jefferson Ave., St. Paul, Minn. 55102

[21] Appl. No.: 4,628

[22] Filed: Jan. 20, 1987

[51] Int. Cl.[4] ...................... H01R 11/11; H01R 13/62
[52] U.S. Cl. .................................... 439/372; 439/725
[58] Field of Search .............. 439/296, 372, 725-729, 439/775, 786-790, 835-838

[56] References Cited

U.S. PATENT DOCUMENTS

| | | | |
|---|---|---|---|
| 1,005,846 | 10/1911 | Kaesen | 439/727 |
| 2,574,043 | 11/1951 | Lannon | 439/729 |
| 2,894,243 | 7/1959 | Hayes | 439/725 |
| 3,725,853 | 4/1973 | McKeown et al. | 439/836 |
| 3,944,313 | 3/1976 | McKeown et al. | 439/836 |
| 4,458,975 | 7/1984 | Bohlin et al. | 439/838 |
| 4,550,961 | 11/1985 | Aicher et al. | 439/836 |

FOREIGN PATENT DOCUMENTS 104641  5/1963  Netherlands ........................ 439/372

*Primary Examiner*—Gil Weidenfeld
*Assistant Examiner*—Gary F. Paumen
*Attorney, Agent, or Firm*—Hugh D. Jaeger

[57] ABSTRACT

Electrode clip for attachment to a TENS electrode or other medical electrode including a slide actuator within a grooved channel for moving longitudinally and rotationally positioning an upper contact body including an integral contact over and about an interceded electrode contact assembly, and securing the electrode contact assembly over a lower contact integral to an electrode clip main body. The sliding actuator includes catches and latches in the sliding actuator and related structure for positioning to actuate and to secure the electrode clip upper contact body in a secured or unsecured position over the main body. Spring contacts in the lower main body contact assembly provide electrical continuity between upper and lower contacts for ensuring electrical contact between the upper and lower contacts and an inserted electrode.

7 Claims, 4 Drawing Sheets

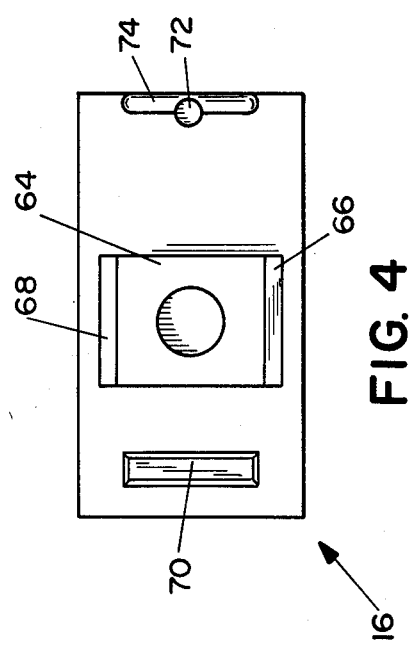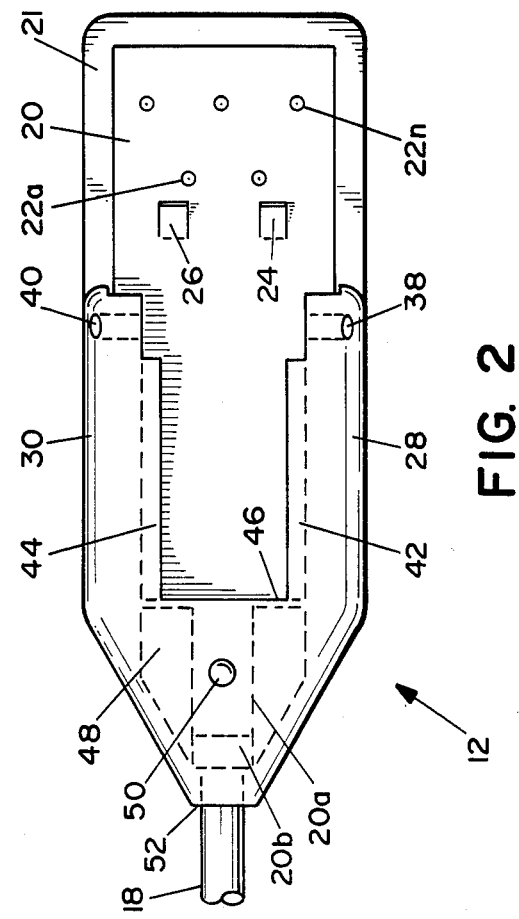

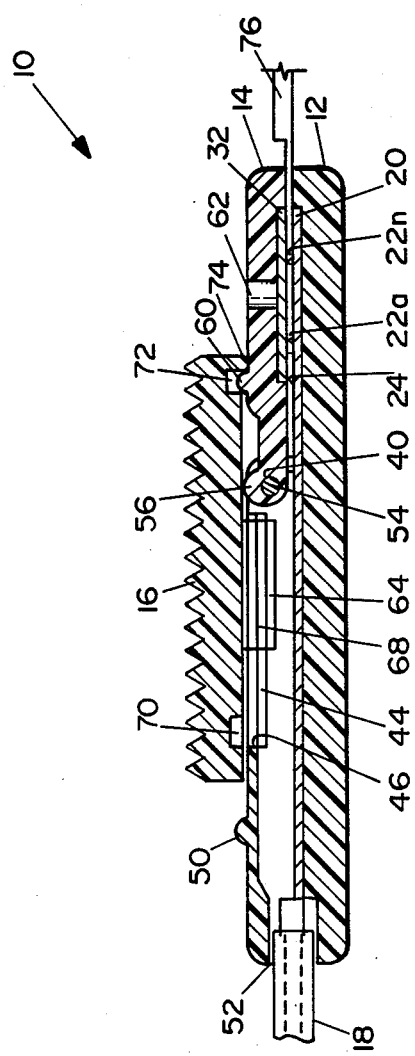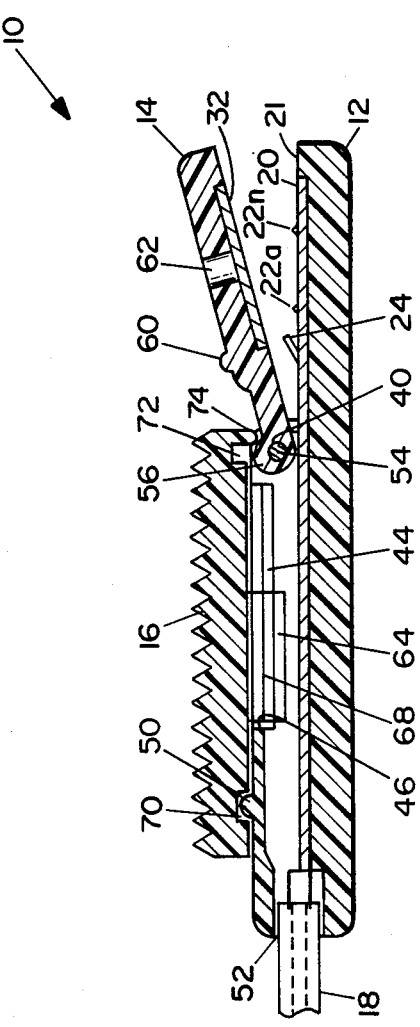

ELECTRODE CLIP

BACKGROUND OF THE INVENTION

1. Field of the Invention

The present invention pertains to an electrode clip and more particularly, pertains to an electrode clip connector including a main body with a slide actuated upper body which engages an electrode contact placed between the main body and upper actuated body.

2. Description of the Prior Art

Prior art clips have been of a high, bulky profile, and were uncomfortable when positioned between a patient and surrounding environment such as a bed or chair. Exposed metallic clip parts of an alligator clip offer the possibility of electrical contact with undesirable electrical sources causing erroneous readings or possible injury to a patient. Springs in prior art clips were subject to weakening, and non-uniform securing tensions.

The present invention overcomes the disadvantages of prior art by providing a simple to use, low profile, electrode clip utilizing a non-conductive plastic body and a slide bar to secure internal insulated contacts to an electrode.

SUMMARY OF THE INVENTION

The general purpose of the present invention is to provide a low profile insulated electrode clip which can be manually operated by positioning a cam actuated upper contact pad with a sliding actuator. A cam bar actuator moves the upper contact pad, by action against a cam bar, about pivot pins to press the upper contact pad against a lower contact pad member and an electrode therebetween. The upper and lower contact pads are integral to the insulated movable clip members. Catches in the slider bar actuator engage latches to hold the clip in either an open or a closed position.

According to one embodiment of the present invention, there is provided an electrode clip including a main body member, an integral contact pad including gripper teeth and spring contacts, raised opposed mirror image like grooved V channel members positioned along portions of the main body, pivot holes positioned in the inner ends of the grooved V channel members, and V channel stops positioned between the interior ends of the V channels. A slide actuator includes a slide base, dual opposing V bars on the slide base, nodule catches at each end, and an actuator bar. An upper contact body includes an upper contact pad, a top positioned latch, pivot assembly and cam bar attached to the upper contact body by a connecting strut and a latch nodule.

One significant aspect and feature of the present invention is an electrode clip with upper and lower contact surfaces for contact with an electrode regardless of the orientation of the electrode.

Another significant feature and aspect of the present invention is an electrode clip which locks using latches and cams in both an open and a closed position.

Still another significant feature and aspect of the present invention is an insulated, low profile body, electrode clip.

Another significant aspect and feature of the present invention is an upper contact connected to the lower contact by spring contactors to provide two surfaces for engaging an electrode.

Having thus described embodiments of the present invention, it is the principal object hereof to provide a low profile insulated electrode clip utilizing a positionable upper contact pad connected to a lower contact pad for connection to an electrode. The electrode can be a TENS electrode, medical electrode or any other like conductive member.

Another object of the present invention is an electrode clip which connects to an electrode regardless of electrode orientation. This is particularly significant for electrodes which are applied to one's body.

Another object of the present invention is an electrode clip utilizing a slide actuator including a portion for engagement by one's finger or thumb.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 2 illustrates a top view of the electrode clip body member;

FIG. 3 illustrates a top view of upper body contact;

FIG. 4 illustrates a bottom view of the slide actuator;

FIG. 6 illustrates a sectional view of the electrode clip in the actuated position taken along line 6—6 of FIG. 1; and, FIG. 7 illustrates a sectional view of the electrode clip of FIG. 6 in the released position.

DESCRIPTION OF THE PREFERRED EMBODIMENTS

Figure 1:
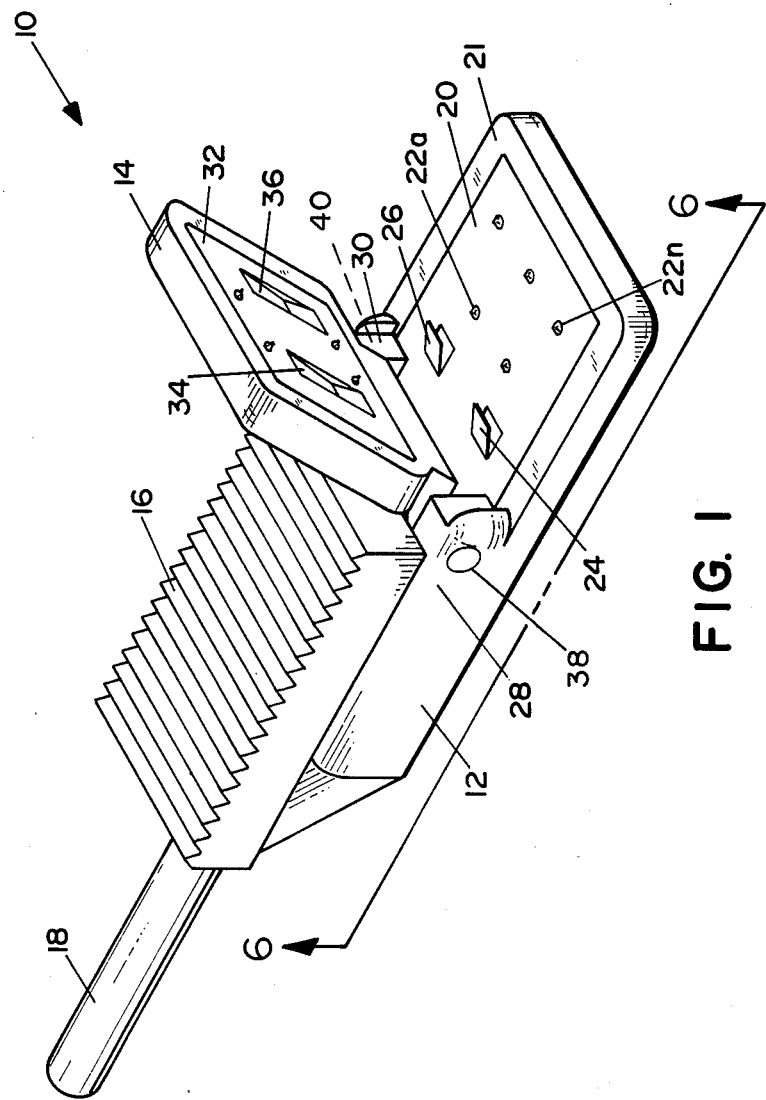
FIG. 1 illustrates a perspective view of an electrode clip, the present invention.

FIG. 1 illustrates a perspective view of an electrode clip 10, the present invention, including an electrode clip body 12, a pivoting upper contact body 14, a grooved slide actuator 16 and an attached insulated wire lead 18. A lower metallic contact pad 20, molded into an upper face 21 of the electrode clip body 12, includes a plurality of gripper teeth 22a-22n and spring contacts 24 and 26. The pivotally mounted upper contact body 14 rotates about a pivot, as later described in detail, within pivot holes 38 and 40 located in the inner faces of main body channel wall members 28 and 30. A metallic upper contact pad 32, integrally molded into the upper contact body 14, includes fixation knockouts 34 and 36. Slide actuator 16 is illustrated holding and locking the upper contact body 14 in the open position. The spring contacts 24 and 26 in the lower contact pad 20 form an electrical contact between the lower contact pad 20 and the upper contact pad 32 when the upper contact body 14 is actuated to the closed position by the slide actuator 16 as illustrated in FIG. 6.

FIG. 2 illustrates a top view of the electrode clip body member 12. Main body channel wall members 28 and 30 include pivot holes 38 and 40 positioned at the inboard ends of the main body channel wall members 28 and 30 as illustrated. V channel grooves 42 and 44 are positioned on the inboard walls of main body channel wall members 28 and 30. A V channel stop 46 is positioned athwart the main body channel wall members 28 and 30 and V channel grooves 42 and 44 adjacent to a triangular shaped end portion 48 of the electode clip body 12. A protruding semi-spherical nodule latch 50, on the triangular shaped end portion 48 of the electrode clip body 12, is positioned for subsequent engagement with a nodule catch of the slide actuator 16 as later described in detail. The lower contact pad 20, on an inner face of the electrode clip body 12, includes a narrow tongue portion 20a and a swedge collar fitting 20b into which the bare end of wire lead 18 is inserted, swedged and soldered for electrical and mechanical integrity of the connection. A hole 52 positions at the apex end of the electrode clip body to accommodate the wire lead 18.

FIG. 3 illustrates a top view of the rectangular shaped upper contact body 14. Pivots 53 and 54 position at the ends of a cam bar 56. A strut member 58 joins the cam bar 56 and pivots 53 and 54 to the rectangular shaped upper contact body 14. A protruding semispherical latch nodule 60 positions on the upper surface and adjacent to the inboard edge of the upper contact body 14. A test probe hole 62 is centrally positioned. Pivots 53 and 54 rotate within pivot holes 38 and 40, respectively.

Figure 5:
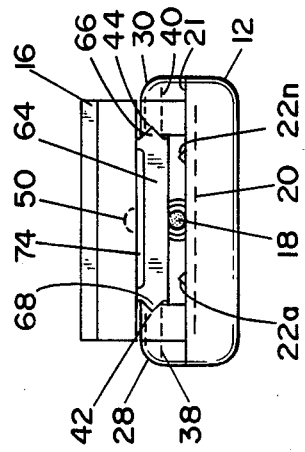
FIG. 5 illustrates an end view of the slide actuator engaged in the electrode clip body member with the upper body contact removed.

FIG. 4 illustrates a bottom view of the slide actuator 16 particularly showing the slide actuator base 64 and V bars 66 and 68, as also illustrated in FIG. 5, which slide longitudinally within the V channel grooves 42 and 44 in the electrode clip body 12. A recessed nodule catch 70 positions as illustrated on the underside in one end of the slide actuator 16. A nodule catch 72 and cam bar 74 position at the opposite end of the slide actuator 16.

FIG. 5 illustrates an end view of the slide actuator 16, in the closed or engaged position with the upper contact body 14 removed for sake of clarity. Shown in particular is the positioning of V bars 66 and 68 within the V channel grooves 44 and 42 providing for sliding motion of the slide actuator 16 in the channel wall members 28 and 30 of the electrode clip body 12.

MODE OF OPERATION

FIG. 6 illustrates a sectional view of the electrode clip 10 taken along line 6—6 of FIG. 1 where the upper body is closed to make contact, and all numerals correspond to those previously described. When the slide actuator 16 and V bars 68 and 66 slide to the right in V channelgrooves 44 and 42, the nodule catch 72 in the slide actuator 16 engages with latch nodule 60, locking the slide actuator 16 in place and also pivoting and holding down the upper contact body 14 and upper contact pad 32 against the electrode clip body 12. The lower contact pad 20, by action of the cam bar 74 against the upper top surface of the upper contact body 14, mechanically grips an electrode 76 inserted between the upper and lower contact pads 32 and 20, respectively. Spring contacts 24 and 26 in the lower contact pad 20 make electrical contact between the lower contact pad 20 and the upper contact pad 32 ensuring electrical contact between the inserted electrode and the wire lead 18 regardless of the orientation of the electrode 76.

A person actuates the electrode clip 10 by placing the electrode 76 between the upper and lower contact pads 32 and 20, and holding the electrode clip body 12 on ones index finger. Then the slide actuator 16 is actuated with one's thumb to open or close the upper contact body to the open or closed position.

FIG. 7 illustrates a sectional view of the electrode clip 10 of FIG. 6 in the released position. As the slide actuator 16 is moved to the extreme left position, the cam bar 74 engages and actuates the cam bar 56 causing rotational movement about the pivot 53 and 54 to move the upper contact body 14 away from the lower contact pad 20 in the electrode clip body 12 for grasping of the electrode 76 between the upper and lower contact pads 32 and 20. Nodule catch 70 engages over and about nodule latch 50 to hold and maintain the upper contact body 14 in an opened position. In the alternative, the pivot pins 53 and 54 could be a continuous metal pin instead of plastic pivot pins as illustrated.

Various modifications can be made to the present invention without departing from the apparent scope thereof. The connector may be available with or without the wire preattached. A contact terminal pin having a nominal outside diameter approximating 0.080" could also be inserted into the hole. In the alternative, instead of using a swedged connection or a terminal pin to fasten the connector to a wire lead, the member can also be molded directly onto the wire.

We claim:

1. An electrode clip for connection to a medical electrode comprising:
   a. a flat main body of insulating material having a first end with an aperture for receiving a connecting wire, a second end with a first flat integral contact pad having a portion thereof extending to said first end for connection to said connecting wire and including first and second opposing channel wall members having V grooves positioned therein;
   b. first and second pivot holes oppositely positioned in said channel wall members;
   c. a plurality of gripper teeth on said first contact pad;
   d. at least one spring contactor on said first contact pad;
   e. a slide actuator having V shaped slide bars positioned for movement along said V grooves between a first open position and a second closed position;
   f. first and second catches at opposing ends of said slide actuator opposite said main body;
   g. a cam bar actuator on a lower forward surface of said slide actuator base;
   h. an upper contact body of insulating material having a second flat integral contact pad including gripper teeth for engagement with an inserted electrode;
   i. first and second pivot pins attached to said upper contact body and adapted to rotate within said pivot holes allowing said spring contactor to electrically connect said first and second contact pads;
   j. a cam bar positioned at an end of said upper contact body for interaction with said cam bar actuator to force said upper contact body towards said main body by rotation about said pivot pins causing said first and second contact pads to engage an electrode inserted therebetween and said spring contactor to electrically connect said first and second contact pads when said slide actuator is moved;
   k. a first latch positioned on said main body adjacent said first end thereof for engagement with said first catch when said slide actuator is in the first, open, position; and,
   l. a second latch positioned on said upper contact body for engagement with said second catch when said slide actuator is in said second, closed, position.

2. The electrode clip of claim 1 wherein said main body and said upper contact body serve to insulate the nonabutting surfaces of said first and second contact pads against accidental contact with the body of a patient.

3. The electrode clip of claim 1 wherein said spring contact is rearwardly positioned to provide electrical connection of said lower contact pad to said upper contact pad.

4. The electrode clip of claim 1 wherein said cam bar opens and holds said upper contact body in said open or closed position.

5. The electrode clip of claim 1 wherein said first and second catches and said first and second latches retain said upper contact body in said closed or open position.

6. The electrode clip of claim 1 wherein said slide actuator moves in said V grooves to position said cam operated upper contact body.

7. The electrode clip of claim 1 wherein said spring contactor is positioned between opposing inner surfaces of said first and second contact pads.

* * * * *